(12) United States Patent
Do et al.

(10) Patent No.: US 6,784,287 B2
(45) Date of Patent: Aug. 31, 2004

(54) ORGANIC DYE MOLECULES AND NONLINEAR OPTICAL POLYMERIC COMPOUNDS CONTAINING CHROMOPHORES

(75) Inventors: Jung Yun Do, Daejon (KR); Myung Hyun Lee, Daejon (KR); Seung Koo Park, Daejon (KR); Jung Jin Ju, Daejon (KR); Suntak Park, Daejon (KR)

(73) Assignee: Electronics and Telecommunications Research Institute, Daejon (KR)

( * ) Notice: Subject to any disclaimer, the term of this patent is extended or adjusted under 35 U.S.C. 154(b) by 0 days.

(21) Appl. No.: 10/085,272

(22) Filed: Feb. 27, 2002

(65) Prior Publication Data
US 2003/0146420 A1 Aug. 7, 2003

(30) Foreign Application Priority Data
Dec. 26, 2001 (KR) ................. 10-2001-0085041

(51) Int. Cl.[7] ............ C09B 23/10; C09B 33/02
(52) U.S. Cl. ......... 534/797; 534/852; 534/855; 534/857; 548/243; 548/444; 558/426; 560/21
(58) Field of Search ............... 534/797, 852, 534/855, 857; 548/243, 244, 444; 558/426; 560/21

(56) References Cited

U.S. PATENT DOCUMENTS

| 4,994,209 A | 2/1991 | Okazaki ............ 252/587 |
| 5,496,899 A | 3/1996 | Foll et al. ......... 525/327.2 |
| 6,229,047 B1 | 5/2001 | Glaser et al. ........ 564/249 |
| 6,429,023 B1 * | 8/2002 | Gharavi ............ 436/167 |

FOREIGN PATENT DOCUMENTS

| KR | 0151906 | 6/1998 |
| KR | 10-0169910 | 10/1998 |

OTHER PUBLICATIONS

Ashworth et al., Chemical Abstracts, 133:89901, 2000.*
"Polymeric Electro–optic Modulators: From Chromophore . . . ", L. Dalton, et al., Ind. Eng. Chem. Res., 1999, 38, 8–33.
"Synthesis and Processing of Improved Organic . . . ", L. Dalton, et al., Chem. Mater., 1995, 7, 1060–1081.

* cited by examiner

Primary Examiner—Fiona T. Powers
(74) Attorney, Agent, or Firm—Blakely, Sokoloff, Taylor & Zafman

(57) ABSTRACT

Organic dye molecular materials prepared by coupling existing organic chromophore molecules to benzene or carbazole derivatives and nonlinear optical polymeric compounds having polyimide repeating units coupled with the organic dye molecular material are provided. The organic dye molecular material coupled to a polymer main chain in the preparation of the nonlinear optical polymeric compound has one of the following formula:

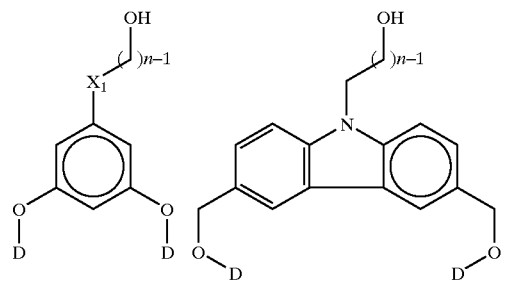

where $X_1$ is carbon, oxygen, sulfur, nitrogen, ester ($CO_2$), or amide ($CONR_1$), where $R_1$ is an alky or phenyl group having 1 to 6 carbon atoms, D is an organic chromophore molecule, and n is an integer from 1 to 10.

3 Claims, 2 Drawing Sheets

ORGANIC DYE MOLECULES AND NONLINEAR OPTICAL POLYMERIC COMPOUNDS CONTAINING CHROMOPHORES

BACKGROUND OF THE INVENTION

1. Field of the Invention

The present invention relates to polymeric compounds with nonlinear optical properties, and more particularly, to organic dye molecular materials and nonlinear optical polymer compounds containing chromophores.

2. Description of the Related Art

Recently, the development of high-speed, high-capacity data transmission devices has increased the need for materials that exhibit nonlinear optical properties and research in this field is being actively performed (Ind. Eng. Chem. Res. 1999, 38, 8–33). These nonlinear optical materials are roughly categorized into inorganic materials such as $LiNbO_3$, KHP, quartz and the like, which have been widely used, and organic materials which become more interesting in the field in recent years along with semiconductor materials. Organic materials are advantageous over inorganic materials in terms of their synthesis and processing procedures and that their physical properties including the processing temperature, refractive index, nonlinear optical coefficient, absorption wavelength and the like can be adjusted according to the requirements. This is the reason why research on the organic material becomes increasing in the field (U.S. Pat. Nos. 5,496,899 and 6,229,047).

Organic materials are classified into crystalline molecules and polymeric substances based on their structure. In the early stage of research, many researchers in a variety of fields were very interested in the crystalline molecule due to its large optical coefficient. However, the crystalline molecule is limited by its unstable nature and difficulties in the crystal growing and processing. To address these limitations, approaches to dispersing organic molecules in polymeric media to develop new materials have been actively made in recent years (Chem. Mater. 1999, 11, 1966–1968). The molecular mobility in a polymeric medium reduces thermal stability and molecular aggregation causes significant optical losses, thereby limiting use of the material.

Meanwhile, to develop materials with desirable processing properties of polymers by incorporating nonlinear organic molecules into polymers is greatly acceptable. Nonlinear polymers are classified into main chains and side chains depending on the way of molecular coupling. Recently, highly ordered macromolecules coupled to be chemically stable, called "dendrimer", have been developed and many approaches have been made to increase their applications (U.S. Pat. Nos. 5,659,010, 5,496,899, and 6,001,958).

In another aspect of research, some researchers are involved in developing new materials based on covalently-bonded film formation technique improved from the Languir-Blodegette (LB) film formation technique. Although it is difficult to obtain a thin film having an appropriate thickness for use with this method, the resulting thin film has a structure highly ordered to give a very large nonlinear coefficient.

For main chain polymers, nonlinear molecular chromophores are directly used as molecules to be polymerized so that the synthesis of the main chain polymer is difficult and the resulting polymer has poor three-dimensional orientation efficiency during a poling process. For side chain polymers, chromophores are grafted to the core as side chains. In this case, although it is difficult to chemically react the polymer, the selection of core polymer is flexible and a variety of chromophores can be incorporated. The ordered arrangement of chromophores on the polymer chain as its side chains is also advantageous.

Dendrimers are sterically highly symmetric and exhibit different characteristics according to their functional end groups incorporated. Also, appropriate designing of a dendrimer molecular structure can separate individual chromophores. When excess chromophores over a predetermined amount are incorporated into a polymeric material, aggregation occurs due to chromophore-chromophore electrostatic interactions, thereby resulting in a low nonlinearity and optical scattering loss due to micro domain. Recent studies evidently show that these problems can be eliminated by using dendrimers (Appl. Phys. Lett. 2000, 77(24), 3881–3883).

Basically, the development of highly nonlinear materials needs highly nonlinear dye molecules. According to recent research results, a nonlinear molecule needs a structure capable of partial electron polarization and a large dipolar moment to provide a large nonlinearity. It is advantageous that the nonlinear molecule has strong electron donor and electron acceptor end groups. In addition, the nonlinear molecule should be extended by conjugated double or triple bonds to allow the electrons, i.e., the $\pi$-electrons, present between the end groups to move freely. It has been also founded that the nonlinearity effect is increased when such conjugated linkages are stably present on the same plane. Some materials with extended $\pi$-linkages to increase their nonlinearity have been reported. As the number of $\pi$-linkages increases, the visible light absorption region of the material where electron transition absorption occurs is gradually shifted to a long-wavelength region. This directly affects on the optical loss by absorption, thereby limiting its use as an optical device material (J. Am. Chem. Soc. 1999, 121, 472–473; Chem. Mater. 1999, 11, 1966–1968). As an example, a wavelength converter or an optical amplifier is often used as a light source of a wavelength of about 600–800 nm. Thus, it is necessary to develop materials that are transparent in this wavelength range for the optical communication device.

Meanwhile, the nonlinearity is directly proportional to the chromophore density in a unit volume. As described above, a high chromophore density over a predetermined range results in a reduced nonlinearly. Therefore, there is a need to increase the chromophore density in a polymeric material without this adverse effect.

SUMMARY OF THE INVENTION

To solve the above-described problems, it is a first objective of the present invention to provide an organic dye molecular material suitable for use in the formulation of an optical polymeric compound having a high nonlinearity.

It is a second objective of the present invention to provide a nonlinear optical polymeric compound for use as an optical device material that comprises molecules capable of absorbing a short-wavelength light, has a high dye molecule density, and is spatially highly ordered to provide a high nonlinearity.

To achieve the first objective of the present invention, there is provided an organic dye molecular material having the following formula:

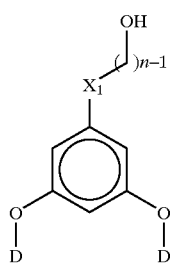

Formula (1)

where $X_1$ is hydrocarbon, oxygen, sulfur, nitrogen, ester ($CO_2$), or amide ($CONR_1$), where $R_1$ is an alky or phenyl group having 1 to 6 carbon atoms, D is an organic chromophore molecule, and n is an integer from 1 to 10.

To achieve the first objective of the present invention, there is provided another organic dye molecular material the following formula:

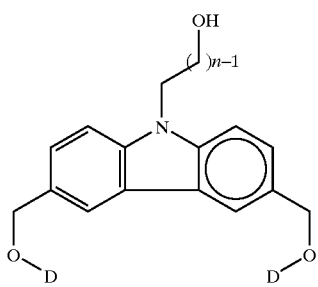

Formula (2)

where D is an organic chromophore molecule, and n is an integer from 1 to 10.

In formulae (1) and (2) above, the organic chromophore molecule D may be any well-known organic chromophore. For example, the organic chromophore molecule D may have a structure selected from structures (A-1), (A-2) and (A-3) in the following formula (3) in which each chromophore molecule is shown as D-OH:

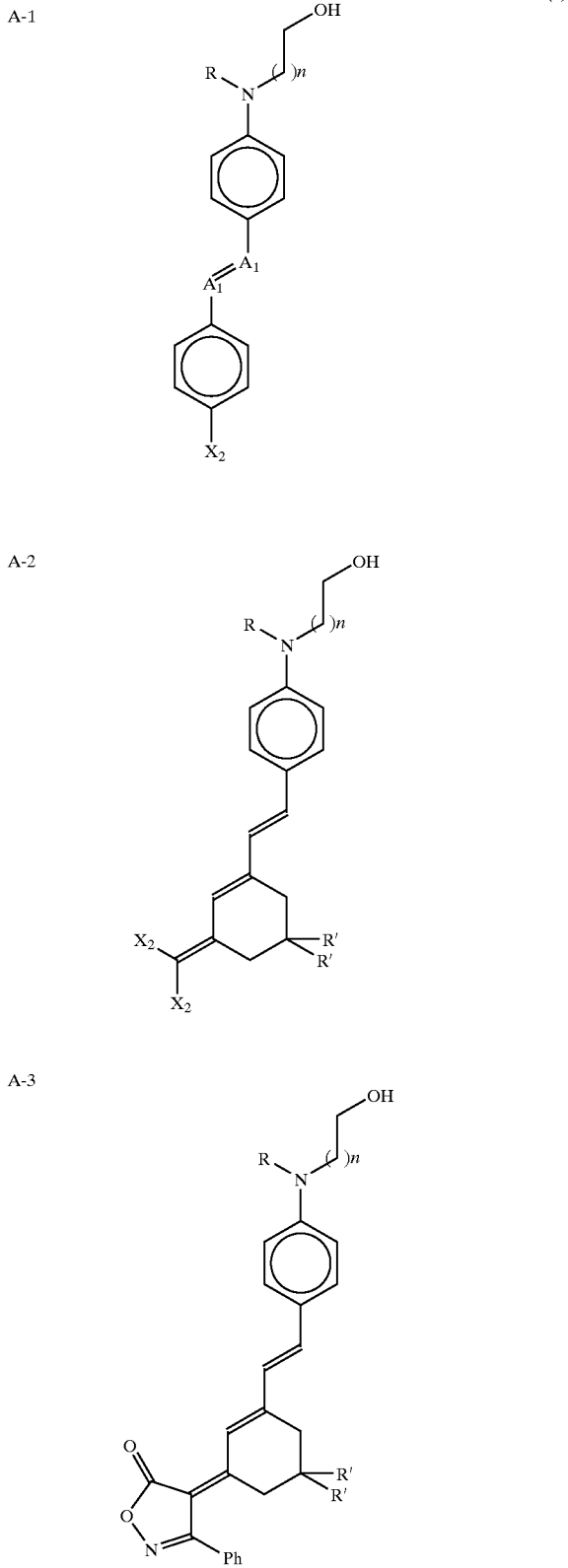

where R and R' are each independently alkyl or phenyl groups having 1 to 10 carbon atoms, $A_1$ is carbon or nitrogen, $X_2$ is $NO_2$, a sulfonyl-substituted or unsubstituted alkyl group having 1 to 10 carbon atoms, CN, —C(CN)═C $(CN)_2$, an ester group, a carbonyl group, a halogen element, or a haloalkyl group, and n is an integer from 1 to 11.

In conjunction with formula (3), typical examples of the organic chromophore molecule having the structure (A-1) include Disperse Red 1 (DR1) series where $R=CH_3CH_2$, $A_1=N$, $X_2=NO_2$, and n=2, dialkylaminophenyl nitrostilbene (DANS) series where $R=CH_3CH_2$, $A_1=CH$, $X_2=NO_2$, and n=2, DASS series where $R=CH_3$ or $CH_3CH_2$, $A_1=CH$, $X_2=SO_2$, and n=2, and the like. A typical example of the organic chromophore molecule having the structure (A-2) includes AIDC derivatives where $R=CH_3CH_2$, $CH_3$, or phenyl, $X_2=CN$, $R'=CH_3$, and n=2.

To achieve the second objective of the present invention, there is provided a nonlinear optical polymeric compound containing polyimide repeating units to which the organic dye molecular material having the formula (1) or (2) above is coupled.

It is preferable that the nonlinear optical polymeric compound according to the present invention comprises a polyimide main chain having formula (4) or (5) below.

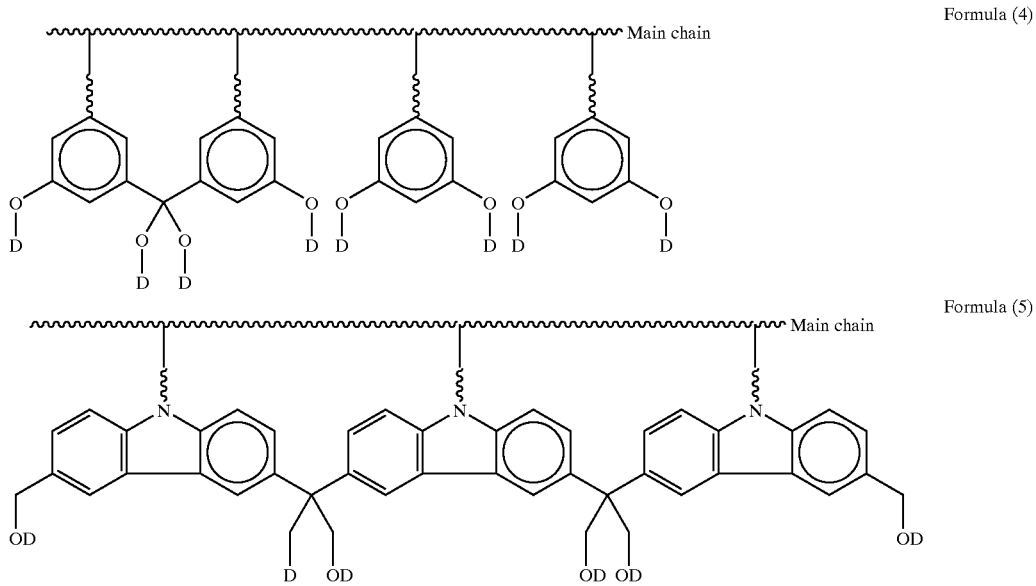

Formula (4)

Formula (5)

The nonlinear optical polymeric compound may have a linear homopolyimide backbone. Alternatively, the nonlinear optical polymeric compound can have a copolymer backbone of polyimide repeating units and other repeating units.

The nonlinear optical polymeric compound preferably have a number average molecular weight of 5,000–500,000.

In the nonlinear optical polymer compound according to the present invention, the polyimide repeating unit preferably has the following formula:

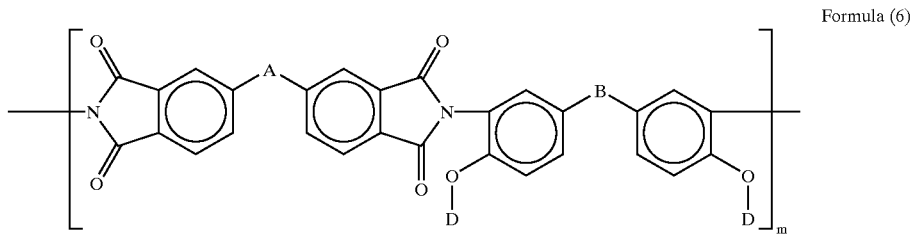

Formula (6)

where A and B are each independently fluorocarbon-substituted or unsubstituted hydrocarbons having 1 to 4 carbon atoms, oxygen, nitrogen, or sulfur, and m is in the range of 0.01 to 1 as the ratio of the polyimide repeating units to all the repeating units of the optical polymeric compound.

More preferably, the polyimide repeating unit has the following formula:

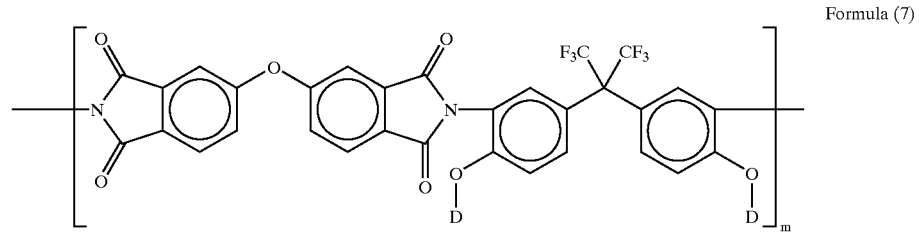

Formula (7)

In the nonlinear optical polymer compound according to the present invention, the amount of the organic chromophore molecule D being coupled to the polyimide repeating unit may be flexibly adjusted. Also, the organic chromophore molecule may be composed of one kind of organic chromophore molecules or different kinds of organic chromophore molecules in a predetermined ratio. Preferably, the polyimide repeating unit contains 10–60% by weight of the organic chromophore molecule D.

According to the present invention, commonly used organic chromophore molecules are coupled into the structure of formula (1) or (2) to give organic dye materials having the new structures. When the organic dye materials according to the present invention are incorporated into optical polymeric compounds, the amount of dye per unit volume of the polymer compound can be highly increased.

The nonlinear optical polymeric compound according to the present invention meets the optical material requirements as the molecular aggregation caused by electrostatic interactions between dye molecules does not occur in the compound at high dye densities. In addition, the optical polymeric compound according to the present invention is suitable for use in the manufacture of an easy-to-manufacture device with excellent physical and chemical stabilities as well as nonlinear optical effects.

BRIEF DESCRIPTION OF THE DRAWINGS

The above objectives and advantages of the present invention will become more apparent by describing in detail preferred embodiments thereof with reference to the attached drawings in which.

DETAILED DESCRIPTION OF THE INVENTION

Figure 1:
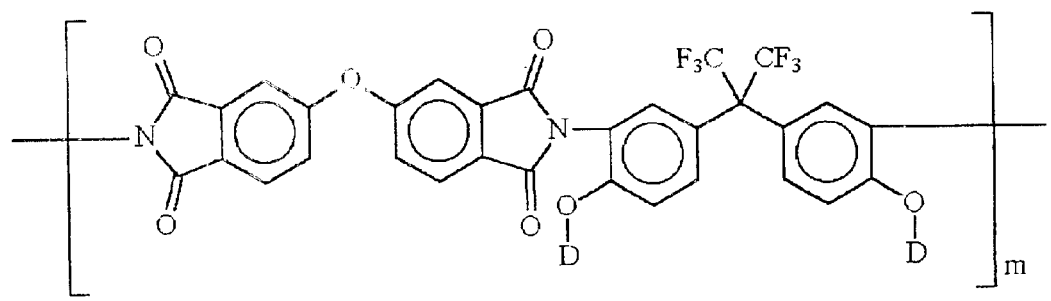
FIG. 1 shows the structure of an optical polymeric compound according to a preferred embodiment of the present invention.

The synthesis path of a first embodiment of an organic dye molecular material according to the present invention is illustrated in Scheme (1) as follows. In Scheme (1), reactions to couple an organic chromophore D using benzene derivative are illustrated.

In Scheme (1), the organic dye molecular material includes the organic chromophore D reacting with and coupled to the 3- and 5-phenolic hydroxyl (—OH) groups of the benzene ring. In forming this structure, an aliphatic hydroxyl group is introduced to allow easy incorporation of the organic chromophore D into the polymer. In particular, an aliphatic alcohol compound (I) is first synthesized using dihydroxybenzoic acid by esterification, a compound (III) having the alcoholic hydroxyl group selectively protected as the acetate group is synthesized via two reaction steps, and an ether-bonded compound (IV) is synthesized using triphenylphosphine ($PPh_3$) and diethyl azodicarboxylate (DEAD) known by the Mitsunobu reaction. Then, the protected hydroxyl group is recovered by deprotection reaction to afford a compound (V).

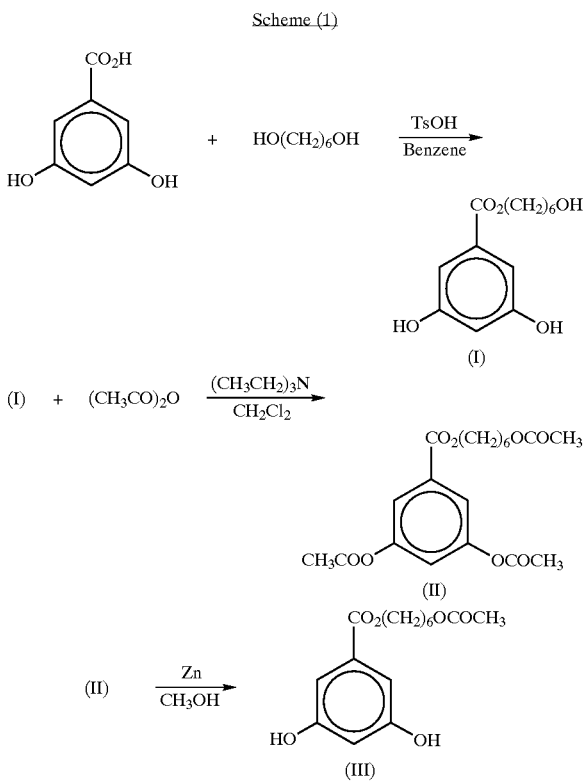

Scheme (1)

-continued

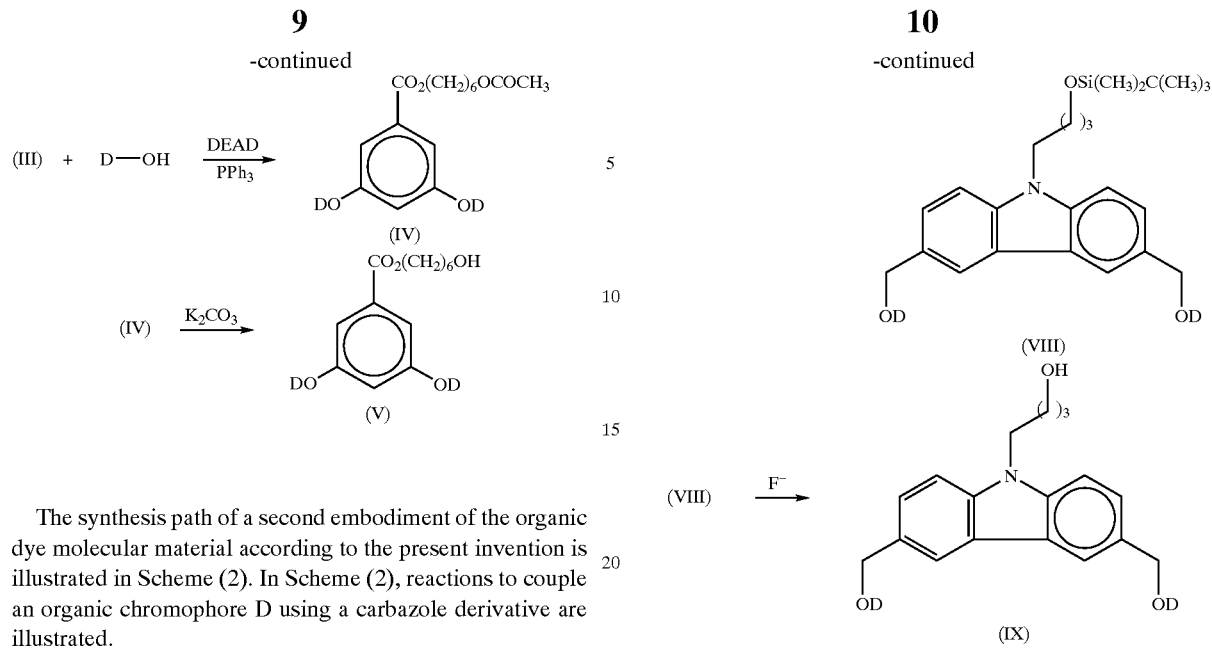

The synthesis path of a second embodiment of the organic dye molecular material according to the present invention is illustrated in Scheme (2). In Scheme (2), reactions to couple an organic chromophore D using a carbazole derivative are illustrated.

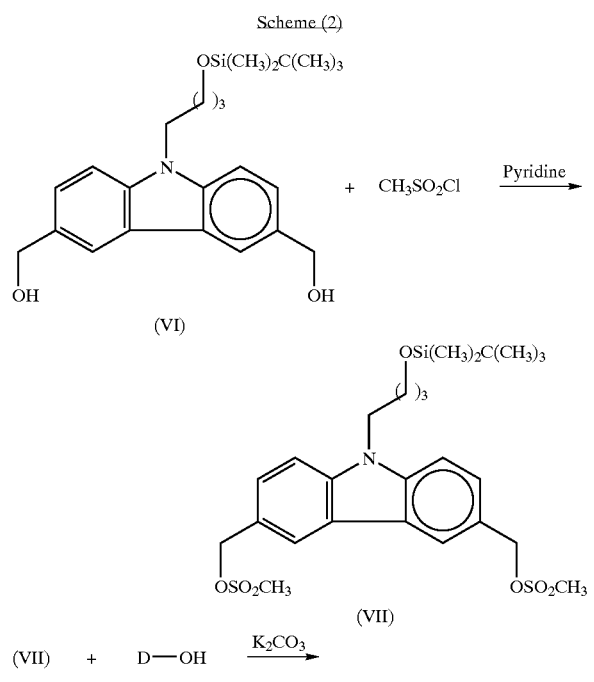

As illustrated in Scheme (2), in coupling the organic chromophore D using the carbazole derivative, one of the three hydroxyl groups of the carbazole derivative is protected as a silicon derivate to couple the organic chromophore D. Methylsulfonyl groups are incorporated to the other two hydroxyl groups to give a compound (VII) and so as to serve as a leaving group in the following ether bonding reaction. Next, the organic chromophore D is coupled, followed by desilylation to afford a compound (IX).

The following Scheme (3) illustrates the synthesis path of an optical polymeric compound by incorporation of the organic dye molecular material obtained through the reactions illustrated in Scheme 1 or 2 into a polyimide backbone.

In Scheme (3), linear polyimide is used as an optical polymer main chain. To incorporate organic chromophore groups as side chains to the polyimide main chain, the Mitsunobu reaction is accomplished using triphenylphosphine (PPh$_3$) and diethyl azodicarboxylate (DEAD). The organic chromophore D is a well-known organic chromophore with maximum absorption at 350~600 nm wavelength.

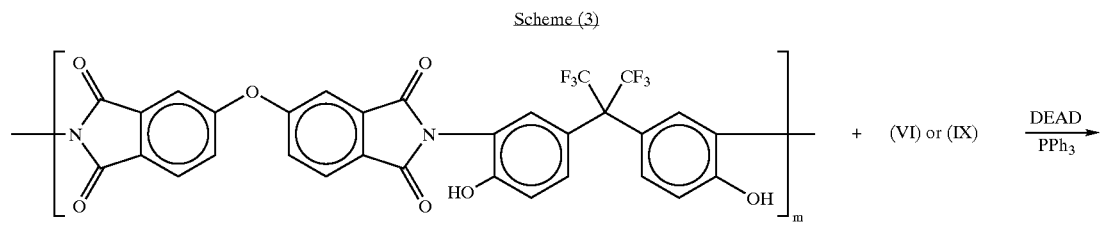

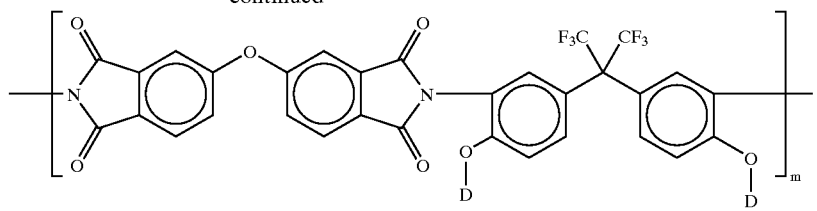

The synthesis reactions illustrated in Schemes (1) through (3) will be described in greater detail by means of the following examples.

EXAMPLE 1

Synthesis of Compound (I)

To a 1-L-2-neck flask containing 400 mL of benzene was added 31 g (0.2 mol) of 3,5-dihydroxybenzoic acid, 71 g (0.6 mol) of 1,6-hexane diol, and 1.9 g (10 mmol) toluene sulfonic acid as a catalyst, and the mixture was vigorously stirred. The reactor was equipped with a Dean-Stark apparatus and the benzene was refluxed for about 6 hours while raising the temperature of the reactor using a thermal coil to remove water. After sufficiently removing the benzene, the organic fraction was dissolved with ethylether, neutralized with aqueous sodium hydrogencarbonate, and washed several times with water. The remaining water was removed from the organic fraction using magnesium sulfate, followed by concentration to obtain a white solid compound. The resulting solid compound was recrystallized using benzene to yield 3,5-dihydroxybenzoic acid ester (I) (47 g, 92%).

$^1$H-NMR (400 MHz; solvent: CDCl$_3$/acetone-d6; δ ppm): 8.26 (d, 2H, —OH), 6.96 (s, 2H), 6.52 (t, 1H), 4.17 (t, 2H), 3.55 (br, 2H), 3.07 (br, 1H, —OH), 1.66 (m, 2H), 1.52 (m, 2H), 1.38 (m, 4H)

$^{13}$C-NMR (solvent: CDCl$_3$/acetone-d6; δ ppm): 166.3, 158.0, 132.1, 108.0, 107.3, 64.7, 62.1, 32.4, 28.4, 25.7, 25.3

EXAMPLE 2

Synthesis of Compound (II)

The 3,5-dihydroxybezoic acid ester (I) obtained from Example 1 was treated with acetic anhydride and triethylamine to protect all the hydroxyl groups as the acetyl groups, affording Compound (II).

EXAMPLE 3

Synthesis of Compound (III)

19 g (0.05 mol) of Compound (II) obtained from Example 2 was dissolved in 150 mL methanol. 6.5 g (0.1 mol) of Zn powder activated with 10%-HCl was added to the solution and stirred vigorously for 12 hours at room temperature. The Zn powder was separated by filtration and the solvent was removed. The resulting product mostly included Compound (III) and a small amount of Compound (I) produced as a result of side reaction. The resulting product may be directly subjected to the next reaction if necessary. In the present example, the resulting product was purified by chromatography on silica gel to remove the by-product, resulting in a high-purity Compound (III).

EXAMPLE 4

Synthesis of Compound (IV)

To couple the organic chromophore to the Compound (III) obtained from Example 3, ester bonding was accomplished using the well-known Mitsunobu reaction. 3.0 g (10 mmol) of the Compound (III), the organic chromophore (AIDC) having the structure (A-2) of formula (3) above, where R and R' are CH$_3$, X$_2$ is CN, and n=2, and 5.8 g (22 mmol) of triphenylphosphine (PPh$_3$) were dissolved in 50 mL anhydrous tetrahydrofuran (THF). 3.5 mL (22 mol) of diethylazodicarbonate (DEAD) was added slowly over 10 minutes while stirring in a nitrogen atmosphere. The mixture was left at room temperature for about 1 hour and concentrated until the volume was reduced to about ⅓, and the concentrate was dropped into ethyl ether to precipitate any residue to yield a red ether solution.

EXAMPLE 5

Synthesis of Compound (V)

The red ether solution obtained from Example 4 was concentrated and dissolved in a mixture of 30 mL methanol and 15 mL THF. 3 g (22 mmol) of grounded potassium carbonate was added to the mixture, vigorously stirred, and left at room temperature for 2 hours. The resulting solution was concentrated, dissolved in 100 mL ethylether, and washed with 200 mL water. The resulting organic fraction was concentrated again, dissolved in about 10 mL anhydrous THF, and recrystallized using 150 mL methanol. The resulting precipitate was filtered and dried in a vacuum to yield Compound V (DAIDC) with a 88% yield.

$^1$H-NMR (400 MHz; solvent: CDCl$_3$; δ ppm): 7.37 (d, 4H), 7.1 (d, 2H), 6.99 (d, 2H), 6.75 (d, 2H), 6.69 (m, 5H), 6.55 (t, 2H), 4.25 (t, 2H), 4.13 (t, 4H), 3.78 (t, 4H), 3.60 (t, 2H), 3.09 (s, 6H), 2.49 (s, 4H), 2.40 (s, 4H), 1.73 (m, 2H), 1.55 (m, 2H), 1.22 (m, 4H), 1.02 (s, 12H)

$^{13}$C-NMR (solvent: CDCl$_3$; δ ppm): 169.1, 166.0, 159.4, 155.2, 150.0, 137.8, 132.3, 129.4, 124.4, 123.8, 121.3, 114.1, 113.3, 111.9, 107.8, 106.2, 75.6, 65.5, 65.1, 62.5, 51.3, 42.8, 39.1, 39.0, 32.4, 31.8, 28.5, 27.9, 25.6, 25.3

EXAMPLE 6

Synthesis of Optical Polymeric Compound

An optical polyimide was synthesized using the polyimide main chain illustrated in Scheme (3) and the organic chromophore (DAIDC) obtained from Example 5 as follows. 1 g of the linear polyimide acting as the main chain for a optical polymeric compound, 3 g (3.3 mmol) of the organic chromophore (DAIDC) and 0.88 g (3.3 mmol) of triphenylphosphine (PPh$_3$) was added to and dissolved in 35 mL anhydrous THF in a nitrogen atmosphere while stirring for 30 minutes. 0.58 g of diethylazodicarbonate (DEAD) was added slowly to the mixture at room temperature and stirred for about 3 hours. 0.44 g of PPh$_3$ and 0.29 g of DEAD were further added and stirred at room temperature for 10 hours. The reaction product was slowly poured into a mixture of 100 mL methanol and 50 mL water to precipitate a polymeric material. The precipitate was filtered and dried. The dried product was dissolved in 25 g of THF and precipitated again using 200 mL methanol. These precipitation and filtration were repeated two times more. The resulting optical polymeric material was vacuum dried at 70° C. for 24 hours to yield dark red powder (3.5 g, 92%).

The maximum UV absorption spectrum of the resulting product was observed at 510 nm and the glass transition temperature (Tg) observed by differential scanning calorimetry (DSC) was 153° C.

EXAMPLE 7

Determination of Optical Polymeric Compound Characteristics 1 g of the optical polymeric material obtained from Example 6 was dissolved in 20 g of a cyclohexanone solvent for about 10 hours to obtain a 15% solution by weight. This solution was passed through a porous filter layer having a 0.2-$\mu$m pore size to remove all small particles. The resulting solution was spin casted on an indium tin oxide (ITO) glass substrate at 1000 rpm for 30 seconds and vacuum dried at 150° C. for 10 hours, resulting in an optical polymer film of a thickness of about 2 mm. An upper surface of the optical polymer film was vacuum deposited with gold (Au) to a thickness of 0.1 $\mu$m to form an upper electrode. The resulting sample device formed of the optical polymeric compound according to the present invention was determined for thermal stability and optical characteristics.

FIG. 1 shows the structure of the optical polymeric compound according to the present invention used in an optical characteristic determination, which will be described below.

Figure 2:
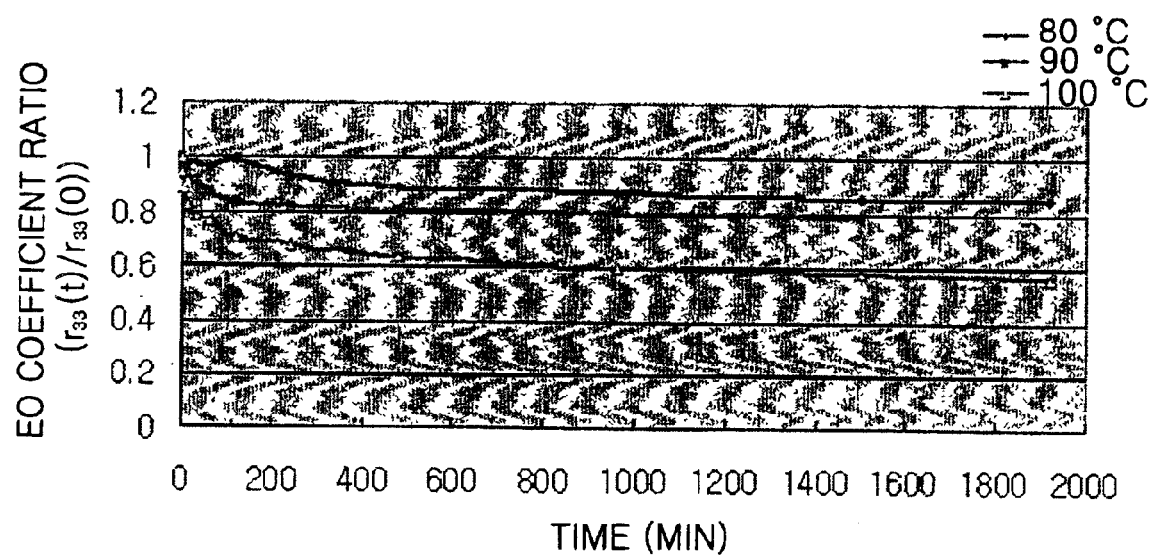
FIG. 2 is a graph showing the thermal stability of a device manufactured from the optical polymeric compound according to the preferred embodiment of the present invention.

FIG. 2 shows the result of a thermal stability test for the optical polymeric compound having the structure of FIG. 1, which was performed on the sample formed in Example 7. For the thermal stability test of the optical polymeric compound having the structure of FIG. 1, variations in electro-optic (EO) coefficient with time were determined at different temperatures. Here, the optical polymeric compound used to form the sample had a glass transition temperature of about 153° C. As is apparent from FIG. 2, the EO coefficient was stably maintained at a temperature of 80° C. after a gentle reduction.

Figure 3:
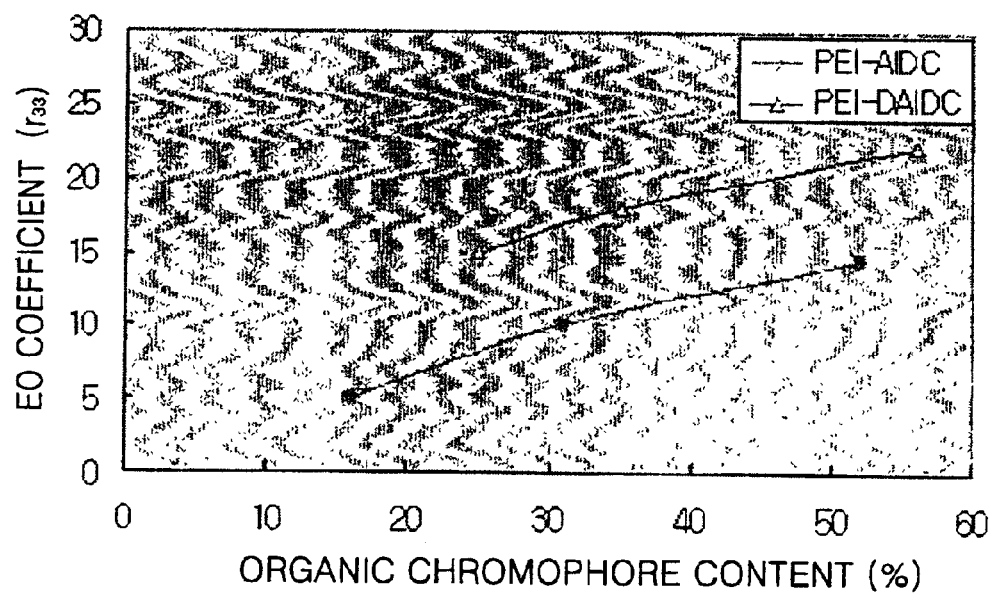
FIG. 3 is a graph showing the result of an optical characteristic determination for a device manufactured from the optical polymeric compound according to the preferred embodiment of the present invention.

FIG. 3 shows the result of an optical characteristic determination for the optical polymeric compound having the structure of FIG. 1 which was performed on the sample formed in Example 7. The organic chromophore D incorporated into the optical polymeric compound having the structure of FIG. 1 is AIDC having the structure (A-2) of formula (3), where R and R' are CH$_3$, X$_2$ is CN, and n=2. As described above, an organic dye molecular material of formula (1) above was synthesized from the organic chromophore D having the structure (A-2) and coupled to a polyimide main chain to give an optical polymer compound (PEI-DAIDC). Then, this optical polymer compound was used to form the sample of Example 7.

For comparison in the optical characteristic determination, a control sample was formed in the same manner as in Example 7 except that an optical polymeric compound (PEI-AIDC) synthesized by coupling the organic chromophore having the structure (A-2) to a polyimide main chain, as described with reference to Scheme (3), was used.

For the sample of Example 7 according to the present invention and the control sample, a variety of polymeric compounds were synthesized by varying the amount of the organic chromophore D being incorporated into each polymeric compound, and the EO coefficients of the polymeric compounds were measured for variations in organic chromophore content. As a result, the EO coefficient was obviously increased with increased amount of the organic chromophore D. In comparing the polymeric compounds PEI-AIDC (control sample) and PEI-DAIDC (present invention), PEI-DAIDC exhibits better nonlinearity than PEI-AIDC at the same organic chromophore contents. It is obvious from this result that the structure of the organic dye molecular material according to the present invention advantageously affects the optical characteristics.

The organic dye molecular material according to the present invention is derived from the coupling of existing organic chromophores to benzene or carbazole derivatives. Also, the optical polymeric compound according to the present invention includes polyimide repeating units to which the organic dye molecular material according to the present invention is coupled. In the structure of the optical polymeric compound according to the present invention, the organic dye molecular material is chemically stably coupled to the polymer main chain. Therefore, the molecular aggregation caused by electrostatic interactions between dye molecules does not occur at high dye densities, which meets the optical material requirements. In addition, the drawback of dendrimers can be improved by substitution of dendrimer-structured molecules into polymers. By adjusting the number of side chains as the organic dye molecular material according to the present invention, physical properties of the resulting optical polymeric compound can be varied so that devices with desired properties can be easily manufactured.

In the optical polymeric compound according to the present invention, a variety of dye molecules, which are well known in the art, are arranged to be spatially efficient to give a high nonlinearity. The optical polymeric compound according to the present invention can absorb a short wavelength of light without having a long $\pi$-electron covalent bond length and thus it exhibits a higher nonlinearity than the conventional optical polymeric compound with directly dye-substituted side chains, at similar dye contents. The structure of the organic dye molecular material according to the present invention is advantageous for optical characteristic improvements.

By adjusting the hydrocarbon chain length of the organic dye molecular material being coupled into an optical polymeric compound according to the present invention, the glass transition temperature of the optical polymeric compound that is an important consideration in the manufacture of optical devices can be controlled. The optical polymeric compound according to the present invention is suitable for use in the manufacture of an easy-to-manufacture device with excellent physical and chemical stabilities as well as nonlinear optical effects.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An organic dye molecular material having the following formula:

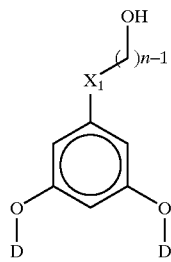

where $X_1$ is hydrocarbon, oxygen, sulfur, nitrogen, ester ($CO_2$), or amide ($CONR_1$), where $R_1$ is an alky or phenyl group having 1 to 6 carbon atoms, D is an organic chromophore molecule, and n is an integer from 1 to 10; wherein the organic chromophore molecule D has a structure selected from the following formula (A-1), (A-2) and (A-3) in which each chromophore molecule is shown as D-OH:

Formula (3)

A-1

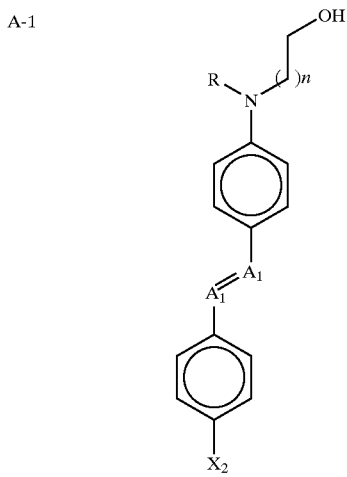

A-2

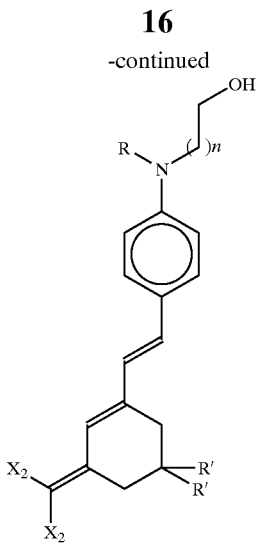

A-3

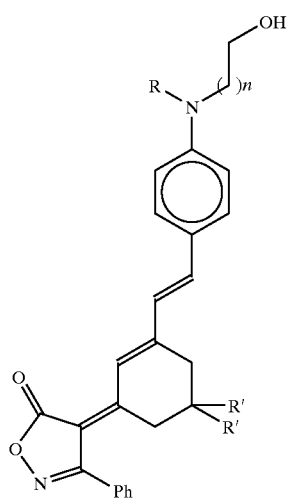

where R and R' are each independently alkyl or phenyl groups having 1 to 10 carbon atoms, $A_1$ is carbon or nitrogen, $X_2$ is $NO_2$, a sulfonyl-substituted or unsubstituted alkyl group having 1 to 10 carbon atoms, CN, —C(CN)=C(CN)$_2$, an ester group, a halogen element, or a haloalkyl group, and n is an integer from 1 to 11.

2. An organic dye molecular material the following formula:

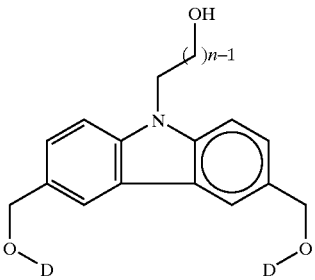

where D is an organic chromophore molecule, and n is an integer from 1 to 10.

3. The organic dye molecular material of claim 2, wherein the organic chromophore molecule D has a structure selected from the following formula (A-1), (A-2) and (A-3) in which each chromophore molecule is shown as D-OH:

A-1 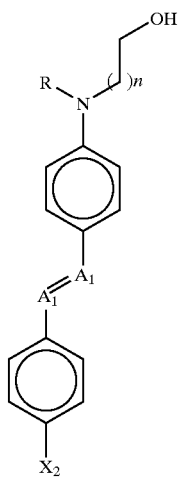
A-2 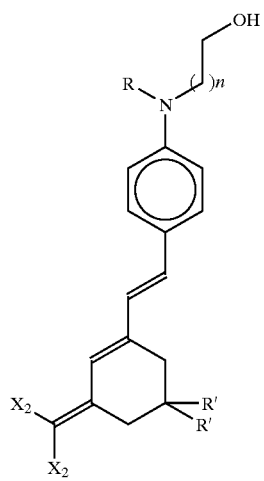
Formula (3)    A-3 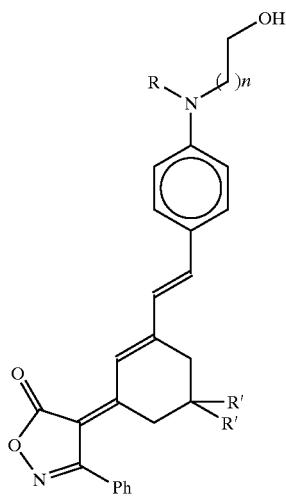
where R and R' are each independently alkyl or phenyl groups having 1 to 10 carbon atoms, $A_1$ is carbon or nitrogen, $X_2$ is $NO_2$, a sulfonyl-substituted or unsubstituted alkyl group having 1 to 10 carbon atoms, CN, —C(CN)=C(CN)$_2$, an ester group, a halogen element, or a haloalkyl group, and n is an integer from 1 to 11.
* * * * *

UNITED STATES PATENT AND TRADEMARK OFFICE
CERTIFICATE OF CORRECTION

PATENT NO.     : 6,784,287 B2
DATED          : August 31, 2004
INVENTOR(S)    : Do et al.

It is certified that error appears in the above-identified patent and that said Letters Patent is hereby corrected as shown below:

Title page,
Item [75], Inventor, please replace "Daejon" with -- Daejeon --
Item [73], Assignee, please replace "Daejon" with -- Daejeon --

Signed and Sealed this

Twenty-ninth Day of March, 2005

JON W. DUDAS
*Director of the United States Patent and Trademark Office*